(12) United States Patent
Odani et al.

(10) Patent No.: US 12,095,036 B2
(45) Date of Patent: Sep. 17, 2024

(54) ELECTROLYTIC SOLUTION FOR LITHIUM-ION SECONDARY BATTERY, AND LITHIUM-ION SECONDARY BATTERY

(71) Applicant: Murata Manufacturing Co., Ltd., Kyoto (JP)

(72) Inventors: Toru Odani, Tokyo (JP); Yoshihide Nagata, Tokyo (JP)

(73) Assignee: Murata Manufacturing Co., Ltd., Kyoto (JP)

(*) Notice: Subject to any disclaimer, the term of this patent is extended or adjusted under 35 U.S.C. 154(b) by 743 days.

(21) Appl. No.: 17/221,402

(22) Filed: Apr. 2, 2021

(65) Prior Publication Data
US 2021/0226253 A1 Jul. 22, 2021

Related U.S. Application Data

(63) Continuation of application No. PCT/JP2019/039059, filed on Oct. 3, 2019.

(30) Foreign Application Priority Data

Oct. 5, 2018 (JP) .................... 2018-190103

(51) Int. Cl.
| | | |
|---|---|---|
| H01M 10/05 | (2010.01) | |
| C07D 319/06 | (2006.01) | |
| C07D 319/08 | (2006.01) | |
| C07D 321/00 | (2006.01) | |
| C07D 321/06 | (2006.01) | |
| C07D 321/10 | (2006.01) | |
| C07D 321/12 | (2006.01) | |

(Continued)

(52) U.S. Cl.
CPC ...... *H01M 10/0567* (2013.01); *C07D 319/06* (2013.01); *C07D 319/08* (2013.01); *C07D 321/00* (2013.01); *C07D 321/06* (2013.01); *C07D 321/10* (2013.01); *C07D 321/12* (2013.01); *H01M 4/364* (2013.01); *H01M 4/386* (2013.01); *H01M 4/587* (2013.01); *H01M 10/0525* (2013.01); *H01M 10/0568* (2013.01); *H01M 10/0569* (2013.01); *H01M 2004/027* (2013.01); *H01M 2300/0025* (2013.01)

(58) Field of Classification Search
None
See application file for complete search history.

(56) References Cited

U.S. PATENT DOCUMENTS

2006/0134527 A1* 6/2006 Amine .............. H01M 10/0567
429/329

FOREIGN PATENT DOCUMENTS

| CN | 101156259 | 4/2008 |
|---|---|---|
| CN | 101438449 | 5/2009 |

(Continued)

OTHER PUBLICATIONS

Chinese Office Action issued Jul. 19, 2023 in corresponding Chinese Application No. 201980065506.1.

(Continued)

*Primary Examiner* — Maria Laios
*Assistant Examiner* — Angela J Martin
(74) *Attorney, Agent, or Firm* — K&L Gates LLP

(57) ABSTRACT

A lithium-ion secondary battery includes a positive electrode, a negative electrode, and an electrolytic solution. The electrolytic solution includes a solvent, an electrolyte salt, and at least one of a first dioxane compound or a second dioxane compound.

9 Claims, 4 Drawing Sheets

(51) Int. Cl.
*H01M 4/36* (2006.01)
*H01M 4/38* (2006.01)
*H01M 4/58* (2010.01)
*H01M 4/587* (2010.01)
*H01M 10/0525* (2010.01)
*H01M 10/0567* (2010.01)
*H01M 10/0568* (2010.01)
*H01M 10/0569* (2010.01)
*H01M 4/02* (2006.01)

(56) References Cited

FOREIGN PATENT DOCUMENTS

| | | | | |
|---|---|---|---|---|
| CN | 103748730 | | 4/2014 | |
| JP | 2003-297421 | A | 10/2003 | |
| JP | 2008-533650 | A | 8/2008 | |
| JP | 2013-065536 | | 4/2013 | |
| JP | 2013-225388 | A | 10/2013 | |
| JP | 2013225388 | * | 10/2013 | .......... H01M 10/052 |

OTHER PUBLICATIONS

Japanese Office Action issued Apr. 26, 2022 in corresponding Japanese Application No. 2020-550530.
International Search Report mailed Dec. 24, 2019 in connection with PCT/JP2019/039059.

* cited by examiner

ELECTROLYTIC SOLUTION FOR LITHIUM-ION SECONDARY BATTERY, AND LITHIUM-ION SECONDARY BATTERY

CROSS REFERENCE TO RELATED APPLICATIONS

The present application is a continuation of PCT patent application no. PCT/JP2019/039059, filed on Oct. 3, 2019, which claims priority to Japanese patent application no. JP2018-190103 filed on Oct. 5, 2018, the entire contents of which are being incorporated herein by reference.

BACKGROUND

The present technology generally relates to: an electrolytic solution to be used for a lithium-ion secondary battery; and a lithium-ion secondary battery including the electrolytic solution.

Various electronic apparatuses such as mobile phones have been widely used. Accordingly, a lithium-ion secondary battery, which is smaller in size and lighter in weight and allows for a higher energy density, is under development as a power source.

The lithium-ion secondary battery includes a positive electrode, a negative electrode, and an electrolytic solution. A configuration of the electrolytic solution greatly influences battery characteristics. Accordingly, various considerations have been given to the configuration of the electrolytic solution. Specifically, to obtain excellent charge and discharge efficiency even at high temperatures, a fluorinated cyclic compound such as 2,2-bis(trifluoromethyl)-1,3-dioxane is included in the electrolytic solution.

SUMMARY

The present technology generally relates to: an electrolytic solution to be used for a lithium-ion secondary battery; and a lithium-ion secondary battery including the electrolytic solution.

Electronic apparatuses, on which a lithium-ion secondary battery is to be mounted, are increasingly gaining higher performance and more functions, causing more frequent use of the electronic apparatuses and expanding a use environment of the electronic apparatuses. Accordingly, there is still room for improvement in terms of battery characteristics of the lithium-ion secondary battery.

The present technology has been made in view of such an issue and it is an object of the technology to provide an electrolytic solution for a lithium-ion secondary battery, and a lithium-ion secondary battery that make it possible to achieve a superior battery characteristic.

An electrolytic solution for a lithium-ion secondary battery according to an embodiment of the technology includes: a solvent; an electrolyte salt; and at least one of a first dioxane compound or a second dioxane compound. The first dioxane compound is represented by Formula (1) below, and the second dioxane compound is represented by Formula (2) below.

Chem. 1

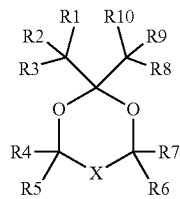

(1)

where:
each of R1 to R10 includes a hydrogen group or a monovalent hydrocarbon group;
and
X includes a divalent hydrocarbon group.

Chem. 2

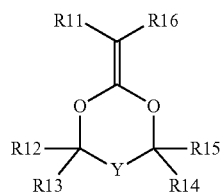

(2)

where:
each of R11 to R16 includes a hydrogen group or a monovalent hydrocarbon group;
and
Y includes a divalent hydrocarbon group.

A lithium-ion secondary battery according to an embodiment of the technology includes a positive electrode, a negative electrode, and an electrolytic solution. The electrolytic solution has a configuration similar to that of the electrolytic solution for a lithium-ion secondary battery according to the embodiment of the technology described herein.

According to the electrolytic solution for a lithium-ion secondary battery, or the lithium-ion secondary battery of the technology, the electrolytic solution includes the first dioxane compound, the second dioxane compound, or both. Accordingly, it is possible to achieve a superior battery characteristic.

It should be understood that effects of the technology are not necessarily limited to those described above and may include any of a series of effects described below in relation to the technology.

DETAILED DESCRIPTION

Figure 1:
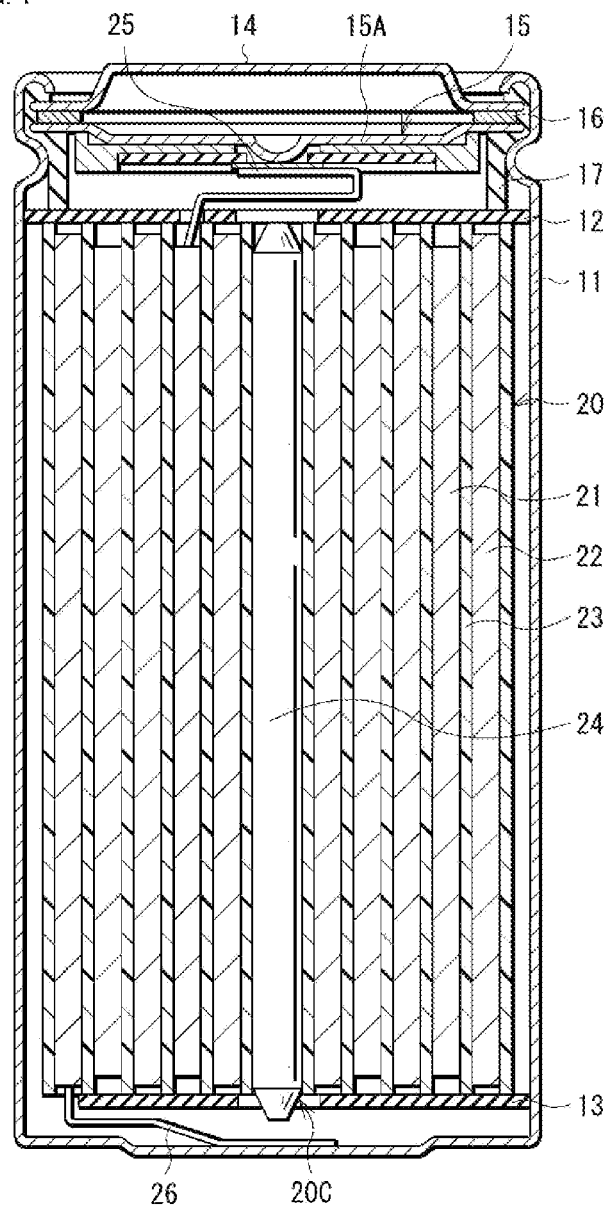
FIG. 1 is a sectional view of a configuration of a lithium-ion secondary battery (cylindrical type) according to an embodiment of the technology.

As described herein, the present disclosure will be described based on examples with reference to the drawings, but the present disclosure is not to be considered limited to the examples, and various numerical values and materials in the examples are considered by way of example.

A description is given first of an electrolytic solution for a lithium-ion secondary battery according to one embodiment of the technology. Hereinafter, the electrolytic solution for a lithium-ion secondary battery according to the embodiment of the technology is simply referred to as an "electrolytic solution".

The lithium-ion secondary battery including the electrolytic solution to be described herein is a secondary battery that obtains a battery capacity by utilizing a lithium insertion phenomenon and a lithium extraction phenomenon, as will be described later.

The electrolytic solution includes a solvent, an electrolyte salt, and a dioxane compound. Only one dioxane compound may be used, or two or more dioxane compounds may be used. In a similar manner, only one solvent may be used, or two or more solvents may be used, and only one electrolyte salt may be used, or two or more electrolyte salts may be used.

The dioxane compound includes a first dioxane compound represented by Formula (1) below, a second dioxane compound represented by Formula (2), or both. Only one first dioxane compound may be used, or two or more first dioxane compounds may be used. In a similar manner, only one second dioxane compound may be used, or two or more second dioxane compounds may be used.

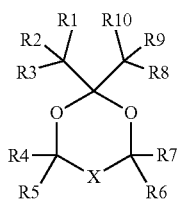

(1)

where:
each of R1 to R10 is a hydrogen group or a monovalent hydrocarbon group; and
X is a divalent hydrocarbon group.

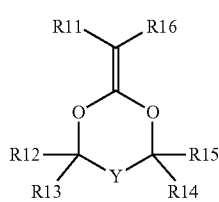

(2)

where:
each of R11 to R16 is a hydrogen group or a monovalent hydrocarbon group; and
Y is a divalent hydrocarbon group.

The first dioxane compound is a compound in which a dioxane skeleton (a cyclic skeleton including two oxygen (O) atoms and X) is substituted by two non-halogenated carbon-containing groups (R1R2R3C— and R8R9R10C—) at position 2, as represented by Formula (1).

The second dioxane compound is a compound in which a dioxane skeleton (a cyclic skeleton including two oxygen atoms and Y) is substituted by one non-halogenated carbon-containing group (R11R16C=C<) at position 2, as represented by Formula (2).

It should be understood that the non-halogenated carbon-containing group described above means a carbon-containing group including no halogen such as fluorine (F) as a constituent element. As described above, the carbon-containing group is each of R1R2R3C— and R8R9R10C— in Formula (1) and is R11R16C=C< in Formula (2).

A reason why the electrolytic solution includes the dioxane compound is that a superior film derived from the dioxane compound is formed on a surface of a negative electrode upon charging and discharging of the lithium-ion secondary battery including the electrolytic solution. In this case, such a film electrochemically protects the surface of the negative electrode. This improves chemical stability of the electrolytic solution, thereby reducing a decomposition reaction of the electrolytic solution. As a result, gas generation due to the decomposition reaction of the electrolytic solution is reduced, and generation of undesired gas is also reduced, thereby suppressing swelling of the lithium-ion secondary battery.

Specifically, each of the following compounds, for example, may be considered as a compound similar to the first dioxane compound. A first example is 1,3-dioxane as represented by Formula (3-1) to be described later. A second example is a compound in which dioxane is substituted by one non-halogenated carbon-containing group (CH$_3$—) at position 2 as represented by Formula (3-2) to be described later. A third example is a compound in which dioxane is substituted by two halogenated carbon-containing groups (CF$_3$— and CF$_3$—) at position 2 as represented by Formula (3-3) to be described later.

1,3-Dioxane represented by Formula (3-1) is a so-called aldehyde protector, thereby having originally low reactivity. In this case, even if a film derived from 1,3-dioxane is formed upon charging and discharging, the film is not easily formed and a quality of the film is insufficient. Accordingly, the decomposition reaction of the electrolytic solution is not sufficiently reduced. As a result, the gas generation due to the decomposition reaction of the electrolytic solution is not reduced, which makes the lithium-ion secondary battery easier to swell.

Such a tendency can be similarly seen in the compound represented by Formula (3-2) in which dioxane is mono-substituted at position 2.

Further, the compound represented by Formula (3-3) in which dioxane is disubstituted at position 2 is not the aldehyde protector, but includes two halogenated carbon-containing groups as described above. In this case, when the compound represented by Formula (3-3) decomposes upon charging and discharging, fluorine-based gas tends to be generated due to a decomposition reaction of the compound. As a result, even if a film is formed, the lithium-ion secondary battery is fundamentally apt to swell due to the fluorine-based gas.

In contrast, unlike the above-described similar compound represented by Formula (3-1) and the above-described similar compound represented by Formula (3-2), the first dioxane compound in which the dioxane skeleton is disubstituted at position 2 is a so-called ketone protector, therefore having originally high reactivity. In this case, when the film derived from the first dioxane compound is formed upon charging and discharging, the film is easily formed and the quality of the film is sufficient, thereby sufficiently reducing the decomposition reaction of the electrolytic solution. As a result, gas generation due to the decomposition reaction of the electrolytic solution is reduced, thereby suppressing swelling of the lithium-ion secondary battery.

Furthermore, unlike the above-described similar compound represented by Formula (3-3), the first dioxane compound does not include the halogenated carbon-containing group. Accordingly, even if the first dioxane compound is decomposed upon charging and discharging, no fluorine-based gas is generated. As a result, there is no fluorine-based gas to promote the swelling of the lithium-ion secondary battery. Accordingly, the swelling of the lithium-ion secondary battery is further suppressed.

It should be noted that the above-described advantages related to the first dioxane compound are also achievable with the second dioxane compound for similar reasons.

Therefore, in the lithium-ion secondary battery in which the electrolytic solution includes the dioxane compound, the decomposition reaction of the electrolytic solution is reduced and the generation of undesired gas is also reduced even if the lithium-ion secondary battery is charged and discharged or stored in a severe environment such as a high-temperature environment. This suppresses the swelling of the lithium-ion secondary battery.

As described above, each of R1 to R10 is not particularly limited as long as each of R1 to R10 is a hydrogen group including no halogen as a constituent element or a monovalent hydrocarbon group including no halogen as a constituent element. It should be understood that any two or more of R1 to R10 may be bonded to each other.

The term "monovalent hydrocarbon group" is a generic term for a monovalent group including carbon (C) and hydrogen (H). The monovalent hydrocarbon group may have: a straight-chain structure: a branched structure having one or more side chains: a cyclic structure; or a structure in a state in which two or more thereof are bonded to each other. The monovalent hydrocarbon group may include, for example, one or more carbon-carbon unsaturated bonds, or may include no carbon-carbon unsaturated bond. The carbon-carbon unsaturated bond includes a carbon-carbon double bond (>C=C<) and a carbon-carbon triple bond (—C≡C—).

Specific examples of the monovalent hydrocarbon group include an alkyl group, an alkenyl group, an alkynyl group, a cycloalkyl group, an aryl group, and a monovalent bonded group. The "monovalent bonded group" is a monovalent group in which two or more of an alkyl group, an alkenyl group, an alkynyl group, a cycloalkyl group, and an aryl group are bonded to each other.

The alkyl group is not limited to a particular kind, and examples thereof include a methyl group, an ethyl group, a propyl group, and a butyl group. The alkenyl group is not limited to a particular kind, and examples thereof include an ethenyl group, a propenyl group, and a butenyl group. The alkynyl group is not limited to a particular kind, and examples thereof include an ethynyl group, a propynyl group, and a butynyl group. The cycloalkyl group is not limited to a particular kind, and examples thereof include a cyclopropyl group, a cyclobutyl group, a cyclopentyl group, and a cyclohexyl group. The aryl group is not limited to a particular kind, and examples thereof include a phenyl group and a naphthyl group. The monovalent bonded group is not limited to a particular kind, and examples thereof include a benzyl group.

The alkyl group has carbon number of less than or equal to 4, and more specifically, from 1 to 4, for example, although the carbon number of the alkyl group is not particularly limited. The alkenyl group and the alkynyl group each have carbon number of less than or equal to 4, and more specifically, from 2 to 4, for example, although the carbon number of each of the alkenyl group and the alkynyl group is not particularly limited. The cycloalkyl group has carbon number from 3 to 6, for example, although the carbon number of the cycloalkyl group is not particularly limited. The aryl group has carbon number from 6 to 14, for example, although the carbon number of the aryl group is not particularly limited. A reason for this is that properties including, without limitation, solubility and compatibility of the first dioxane compound improve.

In particular, it is preferable that the monovalent hydrocarbon group be one of an alkyl group, an alkenyl group, and an alkynyl group. A reason for this is that it is possible to easily synthesize the first dioxane compound and a film is easily formed stably upon charging and discharging. The carbon number of each of the alkyl group, the alkenyl group, and the alkynyl group is as described above.

As described above, X is not particularly limited as long as X is a divalent hydrocarbon group including no halogen as a constituent element.

The term "divalent hydrocarbon group" is a generic term for a divalent group including carbon and hydrogen. The divalent hydrocarbon group may have: a straight-chain structure: a branched structure having one or more side chains; a cyclic structure; or a structure in a state in which two or more thereof are bonded to each other. The divalent hydrocarbon group may include, for example, one or more carbon-carbon unsaturated bonds, or may include no carbon-carbon unsaturated bond.

Specific examples of the divalent hydrocarbon group include an alkylene group, an alkenylene group, an alkynylene group, a cycloalkylene group, an arylene group, and a divalent bonded group. The "divalent bonded group" is a divalent group in which two or more of an alkylene group, an alkenylene group, an alkynylene group, a cycloalkylene group, and an arylene group are bonded to each other.

The alkylene group is not limited to a particular kind, and examples thereof include a methylene group, an ethylene group, a propylene group, and a butylene group. The alkenylene group is not limited to a particular kind, and examples thereof include an ethenylene group, a propenylene group, and a butenylene group. The alkynylene group is not limited to a particular kind, and examples thereof include an ethynylene group, a propynylene group, and a butynylene group. The cycloalkylene group is not limited to a particular kind, and examples thereof include a cyclopropylene group, a cyclobutylene group, a cyclopentylene group, and a cyclohexylene group. The arylene group is not limited to a particular kind, and examples thereof include a phenylene group and a naphthylene group. The divalent bonded group is not limited to a particular kind, and examples thereof include a benzylene group.

The alkylene group has carbon number of less than or equal to 4, and more specifically, from 1 to 4, for example, although the carbon number of the alkylene group is not particularly limited. The alkenylene group and the alkynylene group each have carbon number of less than or equal to 4, and more specifically, from 2 to 4, for example, although the carbon number of each of the alkenylene group and the alkynylene group is not particularly limited. The cycloalkylene group has carbon number from 3 to 6, for example, although the carbon number of the cycloalkylene group is not particularly limited. The arylene group has carbon number from 6 to 14, for example, although the carbon number of the arylene group is not particularly limited. A reason for this is that properties including, without limitation, solubility and compatibility of the second dioxane compound improve.

In particular, it is preferable that the divalent hydrocarbon group be one of an alkylene group, an alkenylene group, and an alkynylene group. A reason for this is that it is possible to easily synthesize the second dioxane compound and a film is easily formed stably upon charging and discharging. The carbon number of each of the alkylene group, the alkenylene group, and the alkynylene group is as described above.

As described above, each of R11 to R16 is not particularly limited as long as each of R11 to R16 is a hydrogen group including no halogen as a constituent element or a monovalent hydrocarbon group including no halogen as a constituent element. As described above, Y is not particularly limited as long as Y is a divalent hydrocarbon group including no halogen as a constituent element. Details of each of the monovalent hydrocarbon group and the divalent hydrocarbon group are as described above. It should be understood that any two or more of R11 to R16 may be bonded to each other.

Specifically, examples of the first dioxane compound include respective compounds represented by Formulae (1-1) to (1-33). Needless to say, specific examples of the first dioxane compound may include other compounds that are not exemplified here as long as they have the structure represented by Formula (1).

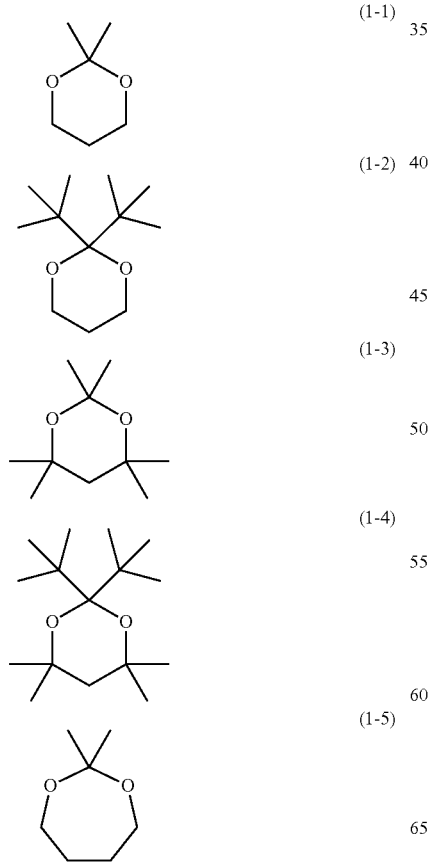

-continued

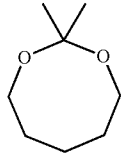 (1-6)

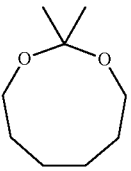 (1-7)

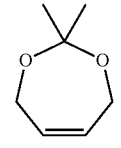 (1-8)

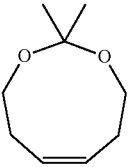 (1-9)

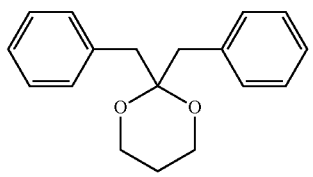 (1-10)

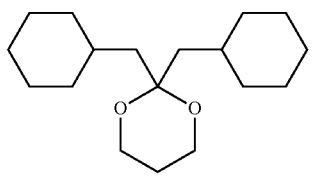 (1-11)

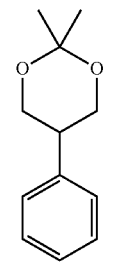 (1-12)

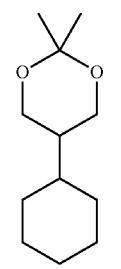 (1-13)

-continued
(1-14)
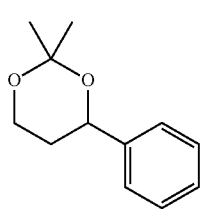
(1-15)
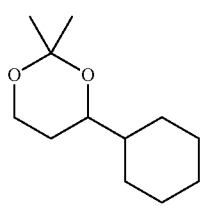
(1-16)
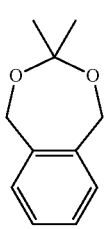
(1-17)
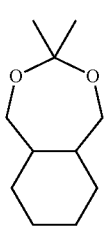
(1-18)
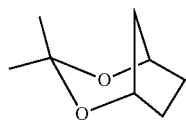
(1-19)
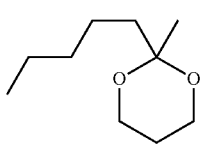
(1-20)
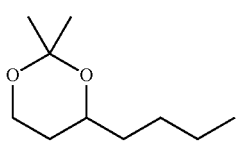
(1-21)
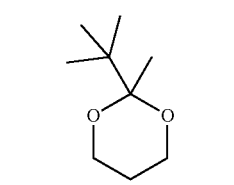
(1-22)
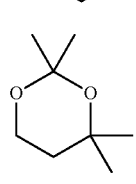
-continued
(1-23)
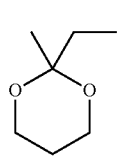
(1-24)
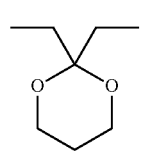
(1-25)
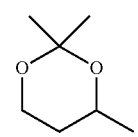
(1-26)
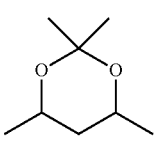
(1-27)
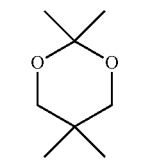
(1-28)
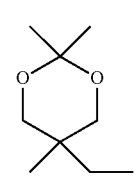
(1-29)
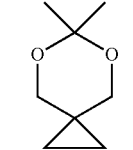
(1-30)
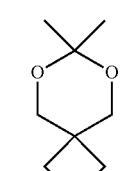
(1-31)
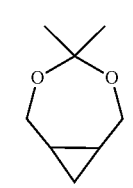

(1-32)
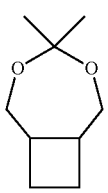
(1-33)
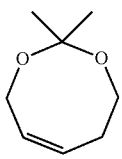
Further, examples of the second dioxane compound include respective compounds represented by Formulae (2-1) to (2-31). Needless to say, specific examples of the second dioxane compound may include other compounds that are not exemplified here as long as they have the structure represented by Formula (2).
(2-1)
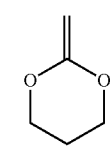
(2-2)
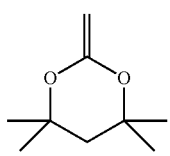
(2-3)
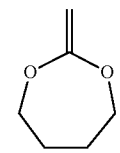
(2-4)
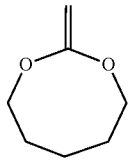
(2-5)
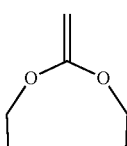
(2-6)
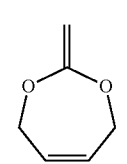
(2-7)
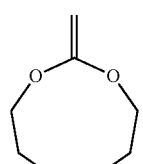
(2-8)
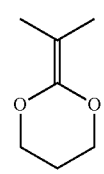
(2-9)
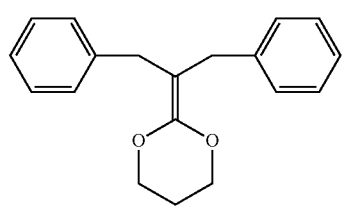
(2-10)
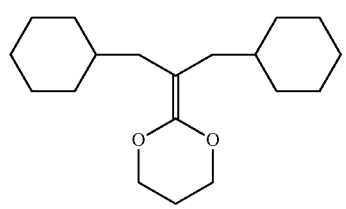
(2-11)
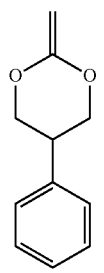
(2-12)
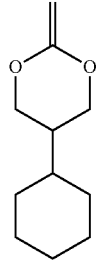
(2-13)

(2-14) 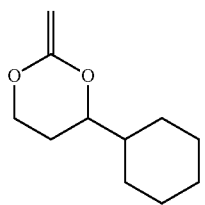
(2-15) 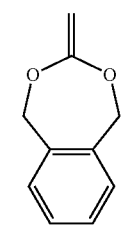
(2-16) 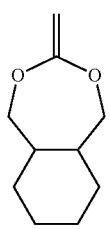
(2-17) 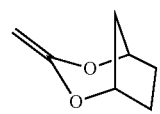
(2-18) 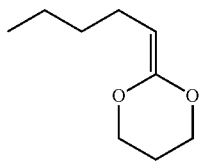
(2-19) 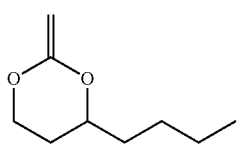
(2-20) 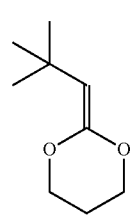
(2-21) 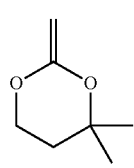
(2-22) 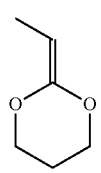
(2-23) 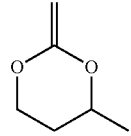
(2-24) 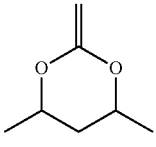
(2-25) 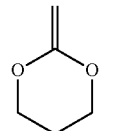
(2-26) 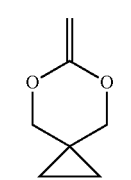
(2-27) 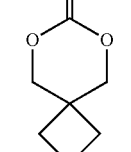
(2-28) 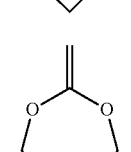
(2-29) 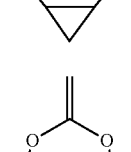
(2-30) 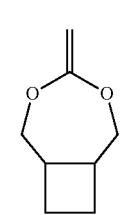

(2-31)

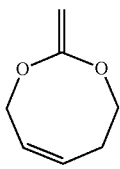

A content of the first dioxane compound in the electrolytic solution is not particularly limited. In particular, the content of the first dioxane compound is preferably greater than or equal to 0.001 wt % and less than or equal to 5 wt %. A reason for this is that properties including, without limitation, the solubility and the compatibility of the first dioxane compound are secured, and also, the decomposition reaction of the electrolytic solution is reduced sufficiently.

A content of the second dioxane compound in the electrolytic solution is not particularly limited. In particular, the content of the second dioxane compound is preferably greater than or equal to 0.001 wt % and less than or equal to 5 wt %. A reason for this is that properties including, without limitation, the solubility and the compatibility of the second dioxane compound are secured, and also, the decomposition reaction of the electrolytic solution is reduced sufficiently.

In a case where the electrolytic solution includes both the first dioxane compound and the second dioxane compound, it is preferable that a sum of the content of the first dioxane compound in the electrolytic solution and the content of the second dioxane compound in the electrolytic solution be within the range described above.

The solvent includes one or more of non-aqueous solvents (organic solvents), for example. An electrolytic solution including the non-aqueous solvent is a so-called non-aqueous electrolytic solution.

The non-aqueous solvent is not limited to a particular kind, and examples thereof include a cyclic carbonate ester, a chain carbonate ester, a lactone, a chain carboxylate ester, and a nitrile (mononitrile) compound. Examples of the cyclic carbonate ester include ethylene carbonate and propylene carbonate. Examples of the chain carbonate ester include dimethyl carbonate and diethyl carbonate. Examples of the lactone include γ-butyrolactone and γ-valerolactone. Examples of the chain carboxylate ester include methyl acetate, ethyl acetate, and methyl propionate. Examples of the nitrile compound include acetonitrile, methoxy acetonitrile, and 3-methoxy propionitrile. A reason for this is that properties including, without limitation, a superior battery capacity, a superior cyclability characteristic, and a superior storage characteristic are achievable.

Examples of the non-aqueous solvent further include an unsaturated cyclic carbonate ester, a halogenated carbonate ester, a sulfonate ester, an acid anhydride, a dicyano compound (a dinitrile compound), a diisocyanate compound, and a phosphate ester. Examples of the unsaturated cyclic carbonate ester include vinylene carbonate, vinyl ethylene carbonate, and methylene ethylene carbonate. Examples of the halogenated carbonate ester include 4-fluoro-1,3-dioxolane-2-one, 4,5-difluoro-1,3-dioxolane-2-one, and fluoromethyl methyl carbonate. Examples of the sulfonate ester include 1,3-propane sultone and 1,3-propene sultone. Examples of the acid anhydride include succinic anhydride, glutaric anhydride, maleic anhydride, ethane disulfonic anhydride, propane disulfonic anhydride, sulfobenzoic anhydride, sulfopropionic anhydride, and sulfobutyric anhydride. Examples of the dinitrile compound include succinonitrile, glutaronitrile, adiponitrile, and phthalonitrile. Examples of the diisocyanate compound include hexamethylene diisocyanate. Examples of the phosphate ester include trimethyl phosphate and triethyl phosphate. A reason for this is that one or more of the series of characteristics described above further improve.

In particular, it is preferable that the non-aqueous solvent include one or more of the unsaturated cyclic carbonate ester, the halogenated carbonate ester, and the dinitrile compound. A reason for this is that properties including, without limitation, a cyclability characteristic further improve.

The electrolyte salt includes one or more of lithium salts, for example. The lithium salt is not limited to a particular kind, and examples thereof include lithium hexafluorophosphate ($LiPF_6$), lithium tetrafluoroborate ($LiBF_4$), lithium bis(fluorosulfonyl)imide ($LiN(SO_2F)_2$), lithium bis(trifluoromethane sulfonyl)imide ($LiN(CF_3SO_2)_2$), lithium fluorophosphate ($LizPFO_3$), lithium difluorophosphate ($LiPF_2O_2$), and lithium bis(oxalato)borate ($LiCABO_8$). A reason for this is that properties including, without limitation, a superior battery capacity, a superior cyclability characteristic, and a superior storage characteristic are achievable.

In particular, it is preferable that the electrolyte salt include one or more of lithium tetrafluoroborate, lithium difluorophosphate, and lithium bis(oxalato)borate. A reason for this is that properties including, without limitation, a cyclability characteristic further improve.

A content of the electrolyte salt is, for example, greater than or equal to 0.3 mol/kg and less than or equal to 3.0 mol/kg with respect to the solvent, but is not particularly limited thereto.

In a case of manufacturing the electrolytic solution, the electrolyte salt is added to the solvent, following which the solvent is stirred. Thus, the electrolyte salt is dispersed or dissolved into the solvent. Thereafter, the dioxane compound is added to the solvent in which the electrolyte salt is dispersed or dissolved, following which the solvent is stirred. The dioxane compound is thereby dispersed or dissolved in the solvent. As described above, the dioxane compound may include only the first dioxane compound, may include only the second dioxane compound, or may include both the first dioxane compound and the second dioxane compound. As a result, the electrolytic solution is obtained that includes the solvent, the electrolyte salt, and the dioxane compound.

The electrolytic solution includes the dioxane compound, i.e., the first dioxane compound, the second dioxane compound, or both. In this case, as described above, it becomes easier to form a superior film as compared with a case where the electrolytic solution includes the similar compound, thereby avoiding generation of the fluorine-based gas and also reducing the decomposition reaction of the electrolytic solution. Accordingly, in the lithium-ion secondary battery including the electrolytic solution, the swelling of the lithium-ion secondary battery is suppressed even if the lithium-ion secondary battery is charged and discharged or stored in a severe environment such as a high-temperature environment. This makes it possible to achieve superior battery characteristics.

It should be understood that the above-described similar compound is each of the respective compounds represented by Formulae (3-1) to (3-3) below. Specifically: the compound represented by Formula (3-1) is 1,3-dioxane; the compound represented by Formula (3-2) is 2-methyl-1,3- dioxane; and the compound represented by Formula (3-3) is 2,2-bis(trifluoromethyl)-1,3-dioxane.

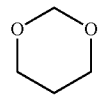

(3-1)

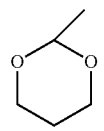

(3-2)

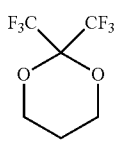

(3-3)

In particular, the monovalent hydrocarbon group related to each of R1 to R16 included in each of Formula (1) and Formula (2) may be a group such as an alkyl group, and the monovalent hydrocarbon group may have carbon number of less than or equal to 4. This secures the solubility and the compatibility of the dioxane compound and also sufficiently reduces the decomposition reaction of the electrolytic solution, which makes it possible to achieve higher effects accordingly. In addition, the divalent hydrocarbon group related to each of X and Y may be a group such as an alkylene group, and the divalent hydrocarbon group may have carbon number of less than or equal to 4. This makes it possible to achieve higher effects accordingly for a similar reason.

Further, the content of the first dioxane compound in the electrolytic solution may be greater than or equal to 0.001 wt % and less than or equal to 5 wt %. This secures the solubility and the compatibility of the first dioxane compound and also sufficiently reduces the decomposition reaction of the electrolytic solution. It is possible to achieve higher effects accordingly. In addition, the content of the second dioxane compound in the electrolytic solution may be greater than or equal to 0.001 wt % and less than or equal to 5 wt %. This makes it possible to achieve higher effects accordingly for a similar reason.

Moreover, the solvent may include materials such as an unsaturated cyclic carbonate ester, and the electrolyte salt may include materials such as lithium tetrafluoroborate. This further improves characteristics such as a cyclability characteristic. It is thus possible to achieve higher effects accordingly.

Next, a description is given of a lithium-ion secondary battery according to one embodiment of the technology including the electrolytic solution described above.

The lithium-ion secondary battery described below includes a positive electrode 21 and a negative electrode 22, which will be described later. The lithium-ion secondary battery obtains, for example, a capacity of the negative electrode 22 by utilizing the lithium insertion phenomenon and the lithium extraction phenomenon.

In such a lithium-ion secondary battery, a charge capacity of the negative electrode 22 is greater than a discharge capacity of the positive electrode 21, in order to prevent unintentional precipitation of lithium metal on a surface of the negative electrode 22 during charging, for example. In other words, an electrochemical capacity per unit area of the negative electrode 22 is greater than an electrochemical capacity per unit area of the positive electrode 21.

A description is given first of a cylindrical lithium-ion secondary battery as an example of the lithium-ion secondary battery.

Figure 2:
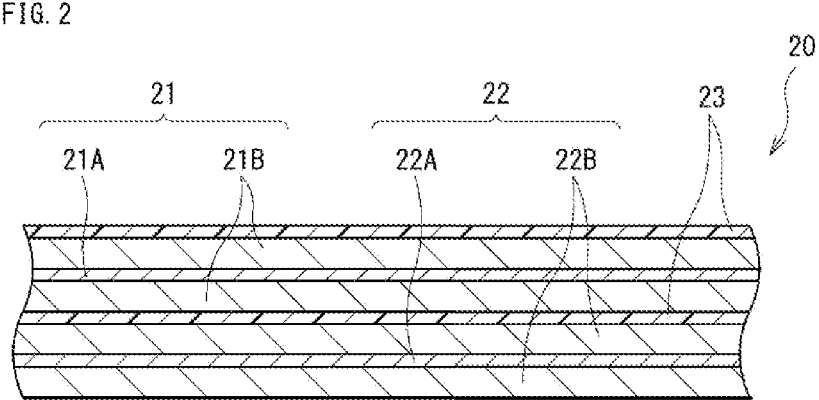
FIG. 2 is an enlarged sectional view of a configuration of a main part of the lithium-ion secondary battery illustrated in FIG. 1.

FIG. 1 illustrates a sectional configuration of the lithium-ion secondary battery. FIG. 2 illustrates, in an enlarged manner, a sectional configuration of a main part, i.e., a wound electrode body 20, of the lithium-ion secondary battery illustrated in FIG. 1. It should be understood that FIG. 2 illustrates only a part of the wound electrode body 20.

Referring to FIG. 1, the lithium-ion secondary battery is provided with a battery can 11 that has a cylindrical shape, for example. The battery can 11 contains the wound electrode body 20, for example. The wound electrode body 20 serves as a battery device.

Specifically, the lithium-ion secondary battery includes a pair of insulating plates 12 and 13 and the wound electrode body 20 that are provided in the battery can 11, for example. The wound electrode body 20 is a structure in which, for example, the positive electrode 21 and the negative electrode 22 are stacked on each other with a separator 23 interposed therebetween, and also in which the stack of the positive electrode 21, the negative electrode 22, and the separator 23 is wound. The wound electrode body 20 is impregnated with an electrolytic solution. The electrolytic solution is a liquid electrolyte.

The battery can 11 has a hollow cylindrical structure having a closed end and an open end, for example. The battery can 11 includes, for example, a metal material such as iron. For example, the battery can 11 has a surface that may be plated with a metal material such as nickel. The insulating plate 12 and the insulating plate 13 are disposed in such a manner as to interpose the wound electrode body 20 therebetween, for example.

A battery cover 14, a safety valve mechanism 15, and a positive temperature coefficient device (PTC device) 16 are crimped at the open end of the battery can 11 by means of a gasket 17, for example, thereby sealing the open end of the battery can 11. The battery cover 14 includes a material similar to a material included in the battery can 11, for example. The safety valve mechanism 15 and the positive temperature coefficient device 16 are each disposed on an inner side of the battery cover 14. The safety valve mechanism 15 is electrically coupled to the battery cover 14 via the positive temperature coefficient device 16. For example, when an internal pressure of the battery can 11 reaches a certain level or higher as a result of causes including, without limitation, internal short circuit and heating from outside, a disk plate 15A inverts in the safety valve mechanism 15, thereby cutting off the electrical coupling between the battery cover 14 and the wound electrode body 20. The positive temperature coefficient device 16 involves an increase in resistance in accordance with a rise in temperature, in order to prevent abnormal heat generation resulting from a large current. The gasket 17 includes an insulating material, for example. The gasket 17 may have a surface on which a material such as asphalt is applied, for example.

A center pin 24 is disposed in a space 20C provided at the winding center of the wound electrode body 20, for example. It should be understood, however, that the center pin 24 may not necessarily be disposed in the space 20C. A positive electrode lead 25 is coupled to the positive electrode 21. The positive electrode lead 25 includes an electrically conductive material such as aluminum. The positive electrode lead 25 is electrically coupled to the battery cover 14 via the safety valve mechanism 15, for example. A negative electrode lead 26 is coupled to the negative electrode 22. The negative electrode lead 26 includes an electrically conductive material such as nickel. The negative electrode lead 26 is electrically coupled to the battery can 11, for example.

As illustrated in FIG. 2, the positive electrode 21 includes, for example, a positive electrode current collector 21A, and a positive electrode active material layer 21B provided on the positive electrode current collector 21A. The positive electrode active material layer 21B may be provided, for example, only on one side of the positive electrode current collector 21A, or on each of both sides of the positive electrode current collector 21A. FIG. 2 illustrates a case where the positive electrode active material layer 21B is provided on each of both sides of the positive electrode current collector 21A, for example.

The positive electrode current collector 21A includes, for example, an electrically conductive material such as aluminum. The positive electrode active material layer 21B includes, as a positive electrode active material or positive electrode active materials, one or more of positive electrode materials into which lithium is insertable and from which lithium is extractable. The positive electrode active material layer 21B may further include one or more of other materials, examples of which include a positive electrode binder and a positive electrode conductor.

The positive electrode material includes a lithium compound, for example. The term "lithium compound" is a generic term for a compound that includes lithium as a constituent element. A reason for this is that a high energy density is achievable. The lithium compound is not limited to a particular kind, and examples thereof include a lithium composite oxide and a lithium phosphate compound.

The lithium composite oxide is an oxide that includes, as constituent elements, lithium and one or more of other elements. The lithium composite oxide has any of crystal structures including, without limitation, a layered rock-salt crystal structure and a spinel crystal structure, for example. The lithium phosphate compound is a phosphate compound that includes, as constituent elements, lithium and one or more of the other elements. The lithium phosphate compound has a crystal structure such as an olivine crystal structure, for example.

The other elements are elements other than lithium. The other elements are not limited to particular kinds; however, it is preferable that the other elements belong to groups 2 to 15 in the long periodic table of elements, in particular. A reason for this is that a higher voltage is obtainable. Specific examples of the other elements include nickel, cobalt, manganese, and iron.

Examples of the lithium composite oxide having the layered rock-salt crystal structure include $LiNiO_2$, $LiCoO_2$, $LiCo_{0.98}Al_{0.01}Mg_{0.01}O_2$, $LiNi_{0.5}Co_{0.2}Mn_{0.3}O_2$, $LiNi_{0.8}Co_{0.15}Al_{0.05}O_2$, $LiNi_{0.33}Co_{0.33}Mn_{0.33}O_2$, $Li_{1.2}Mn_{0.52}Co_{0.175}Ni_{0.1}O_2$, and $Li_{1.15}(Mn_{0.65}Ni_{0.22}Co_{0.13})O_2$. Examples of the lithium composite oxide having the spinel crystal structure include $LiMn_2O_4$. Examples of the lithium phosphate compound having the olivine crystal structure include $LiFePO_4$, $LiMnPO_4$, $LiMn_{0.5}Fe_{0.5}PO_4$, $LiMn_{0.7}Fe_{0.3}PO_4$, and $LiMn_{0.75}Fe_{0.25}PO_4$.

The positive electrode binder includes materials including, without limitation, a synthetic rubber and a polymer compound, for example. Examples of the synthetic rubber include a styrene-butadiene-based rubber. Examples of the polymer compound include polyvinylidene difluoride and polyimide.

The positive electrode conductor includes, for example, an electrically conductive material such as a carbon material. Examples of the carbon material include graphite, carbon black, acetylene black, and Ketjen black. The positive electrode conductor may include a material such as a metal material or an electrically conductive polymer.

As illustrated in FIG. 2, the negative electrode 22 includes, for example, a negative electrode current collector 22A, and a negative electrode active material layer 22B provided on the negative electrode current collector 22A. The negative electrode active material layer 22B may be provided, for example, only on one side of the negative electrode current collector 22A, or on each of both sides of the negative electrode current collector 22A. FIG. 2 illustrates a case where the negative electrode active material layer 22B is provided on each of both sides of the negative electrode current collector 22A, for example.

The negative electrode current collector 22A includes, for example, an electrically conductive material such as copper. It is preferable that the negative electrode current collector 22A have a surface roughened by a method such as an electrolysis method. A reason for this is that improved adherence of the negative electrode active material layer 22B to the negative electrode current collector 22A is achievable by utilizing an anchor effect.

The negative electrode active material layer 22B includes, as a negative electrode active material or negative electrode active materials, one or more of negative electrode materials into which lithium is insertable and from which lithium is extractable. The negative electrode active material layer 22B may further include another material, examples of which include a negative electrode binder and a negative electrode conductor.

Examples of the negative electrode materials include a carbon material and a metal-based material.

The term "carbon material" is a generic term for a material including carbon as a constituent element. A reason for this is that a high energy density is stably obtainable owing to the crystal structure of the carbon material which hardly varies upon insertion and extraction of lithium. Another reason is that an improved electrically conductive property of the negative electrode active material layer 22B is achievable owing to the carbon material which also serves as the negative electrode conductor.

Specific examples of the carbon material include graphitizable carbon, non-graphitizable carbon, and graphite. Spacing of a (002) plane of the non-graphitizable carbon is, for example, greater than or equal to 0.37 nm, and spacing of a (002) plane of the graphite is, for example, smaller than or equal to 0.34 nm.

More specific examples of the carbon material include pyrolytic carbons, cokes, glassy carbon fibers, an organic polymer compound fired body, activated carbon, and carbon blacks. Examples of the cokes include pitch coke, needle coke, and petroleum coke. The organic polymer compound fired body is a resultant of firing or carbonizing a polymer compound such as a phenol resin or a furan resin at any temperature. Other than the above, the carbon material may be low-crystalline carbon heat-treated at a temperature of about 1000° C. or lower, or may be amorphous carbon, for example. The carbon material has a shape such as a fibrous shape, a spherical shape, a granular shape, or a scale-like shape.

The term "metal-based material" is a generic term for a material including one or more of metal elements and metalloid elements as a constituent element or constituent elements. A reason for this is that a high energy density is achievable.

The metal-based material may be a simple substance, an alloy, a compound, a mixture of two or more thereof, or a material including one or more phases thereof. It should be understood that the term "alloy" encompasses not only a material that includes two or more metal elements but also a material that includes one or more metal elements and one or more metalloid elements. The alloy may further include one or more non-metallic elements. The metal-based material has a state such as a solid solution, a eutectic (a eutectic mixture), an intermetallic compound, or a state including two or more thereof that coexist.

The metal element and the metalloid element are each able to form an alloy with lithium. Specific examples of the metal element and the metalloid element include magnesium, boron, aluminum, gallium, indium, silicon, germanium, tin, lead, bismuth, cadmium, silver, zinc, hafnium, zirconium, yttrium, palladium, and platinum.

Among the above-described materials, silicon or tin is preferable, and silicon is more preferable. A reason for this is that a markedly high energy density is obtainable owing to superior lithium insertion capacity and superior lithium extraction capacity thereof. Hereinafter, a material including silicon as a constituent element is referred to as a silicon-containing material, and a material including tin as a constituent element is referred to as a tin-containing material.

Specifically, the silicon-containing material may be a simple substance of silicon, a silicon alloy, a silicon compound, a mixture of two or more thereof, or a material including one or more phases thereof. The simple substance described here merely refers to a simple substance in a general sense. The simple substance may therefore include a small amount of impurity, that is, does not necessarily have a purity of 100%.

The silicon alloy includes, as a constituent element or constituent elements other than silicon, for example, one or more of tin, nickel, copper, iron, cobalt, manganese, zinc, indium, silver, titanium, germanium, bismuth, antimony, and chromium. The silicon compound includes, as a constituent element or constituent elements other than silicon, for example, one or more of materials including, without limitation, carbon and oxygen. The silicon compound may include, as a constituent element or constituent elements other than silicon, any of the constituent elements described in relation to the silicon alloy, for example.

Specific examples of the silicon alloy and the silicon compound include $SiB_4$, $SiB_6$, $Mg_2Si$, $Ni_2Si$, $TiSi_2$, $MoSi_2$, $CoSi_2$, $NiSi_2$, $CaSi_2$, $CrSi_2$, $CuSi$, $FeSi_2$, $MnSi_2$, $NbSi_2$, $TaSi_2$, $VSi_2$, $WSi_2$, $ZnSi_2$, $SiC$, $SiSN_4$, $Si_2N_2O$, and $SiO_v$ (where $0<v\leq2$). It should be understood, however, that a range of "v" may be $0.2<v<1.4$, in one example.

The tin-containing material may be a simple substance of tin, a tin alloy, a tin compound, a mixture of two or more thereof, or a material including one or more phases thereof.

The tin alloy includes, as a constituent element or constituent elements other than tin, for example, one or more of silicon, nickel, copper, iron, cobalt, manganese, zinc, indium, silver, titanium, germanium, bismuth, antimony, and chromium. The tin compound includes, as a constituent element or constituent elements other than tin, for example, one or more of materials including, without limitation, carbon and oxygen. The tin compound may include, as a constituent element or constituent elements other than tin, any of the constituent elements described in relation to the tin alloy, for example.

Specific examples of the tin alloy and the tin compound include $SnO_w$ (where $0<w\leq2$), $SnSiO_3$, and $Mg_2Sn$.

Details of the negative electrode binder are similar to those of the positive electrode binder, for example. Details of the negative electrode conductor are similar to those of the positive electrode conductor, for example.

(Method of Forming Negative Electrode Active Material Layer)

A method of forming the negative electrode active material layer 22B is not particularly limited, and examples thereof include a coating method, a vapor-phase method, a liquid-phase method, a thermal spraying method, and a firing (sintering) method. For example, the coating method involves coating the negative electrode current collector 22A with a solution in which a mixture of materials including, without limitation, a particulate or powdered negative electrode active material and the negative electrode binder is dispersed or dissolved in a solvent such as an organic solvent. Examples of the vapor-phase method include a physical deposition method and a chemical deposition method. More specific examples of the vapor-phase method include a vacuum deposition method, a sputtering method, an ion plating method, a laser ablation method, a thermal chemical vapor deposition method, a chemical vapor deposition (CVD) method, and a plasma chemical vapor deposition method. Examples of the liquid-phase method include an electrolytic plating method and an electroless plating method. The thermal spraying method involves spraying a fused or semi-fused negative electrode active material onto the negative electrode current collector 22A. The firing method involves applying a solution onto the negative electrode current collector 22A by the coating method, and thereafter subjecting the applied solution (a coating) to heat treatment at a temperature higher than a melting point of a material such as the negative electrode binder, for example. More specific examples of the firing method include an atmosphere firing method, a reactive firing method, and a hot-press firing method.

The separator 23 includes a porous film of a material such as a synthetic resin or ceramic, for example. The separator 23 may be a stacked film including two or more porous films that are stacked on each other, in one example. Examples of the synthetic resin include polyethylene.

In particular, the separator 23 may include the porous film and a polymer compound layer, for example. The porous film serves as a base layer. The polymer compound layer is provided on one side or on each of both sides of the base layer, for example. A reason for this is that adherence of the separator 23 to the positive electrode 21 improves and adherence of the separator 23 to the negative electrode 22 also improves to suppress distortion of the wound electrode body 20. This reduces a decomposition reaction of the electrolytic solution and also reduces leakage of the electrolytic solution with which the base layer is impregnated.

The polymer compound layer includes a polymer compound such as polyvinylidene difluoride, for example. A reason for this is that such a polymer compound has superior physical strength and is electrochemically stable. For example, the polymer compound layer may include insulating particles such as inorganic particles. A reason for this is that safety improves. The inorganic particles are not limited to a particular kind, and examples thereof include aluminum oxide and aluminum nitride.

The wound electrode body 20 is impregnated with the electrolytic solution, as described above. Accordingly, the separator 23 is impregnated with the electrolytic solution, and the positive electrode 21 and the negative electrode 22 are also each impregnated with the electrolytic solution, for example. A configuration of the electrolytic solution is as described above.

Upon charging the lithium-ion secondary battery, for example, lithium ions are extracted from the positive electrode 21, and the extracted lithium ions are inserted into the negative electrode 22 via the electrolytic solution. Upon discharging the lithium-ion secondary battery, for example, lithium ions are extracted from the negative electrode 22, and the extracted lithium ions are inserted into the positive electrode 21 via the electrolytic solution.

The lithium-ion secondary battery is manufactured by the following procedure, for example. Fabrication of the positive electrode 21 and fabrication of the negative electrode 22 are performed, following which assembly of the lithium-ion secondary battery is performed. The description on the procedure of the preparation of the electrolytic solution has already been written above, and hence will be omitted here.

First, the positive electrode active material is mixed with materials including, without limitation, the positive electrode binder and the positive electrode conductor on an as-needed basis to thereby obtain a positive electrode mixture. Thereafter, the positive electrode mixture is dispersed or dissolved into a solvent such as an organic solvent or an aqueous solvent to thereby prepare a paste positive electrode mixture slurry. Lastly, the positive electrode mixture slurry is applied on both sides of the positive electrode current collector 21A, following which the applied positive electrode mixture slurry is dried to thereby form the positive electrode active material layers 21B. Thereafter, the positive electrode active material layers 21B may be compression-molded by means of a machine such as a roll pressing machine. In this case, the positive electrode active material layers 21B may be heated. The positive electrode active material layers 21B may be compression-molded a plurality of times.

The negative electrode active material layers 22B are formed on both sides of the negative electrode current collector 22A by a procedure similar to the fabrication procedure of the positive electrode 21 described above. Specifically, the negative electrode active material is mixed with materials including, without limitation, the negative electrode binder and the negative electrode conductor on an as-needed basis to thereby obtain a negative electrode mixture. Thereafter, the negative electrode mixture is dispersed or dissolved into a solvent such as an organic solvent or an aqueous solvent to thereby prepare a paste negative electrode mixture slurry. Thereafter, the negative electrode mixture slurry is applied on both sides of the negative electrode current collector 22A, following which the applied negative electrode mixture slurry is dried to thereby form the negative electrode active material layers 22B. Thereafter, the negative electrode active material layers 22B may be compression-molded.

First, the positive electrode lead 25 is coupled to the positive electrode current collector 21A by a method such as a welding method, and the negative electrode lead 26 is coupled to the negative electrode current collector 22A by a method such as a welding method. Thereafter, the positive electrode 21 and the negative electrode 22 are stacked on each other with the separator 23 interposed therebetween, following which the positive electrode 21, the negative electrode 22, and the separator 23 are wound to thereby form a wound body. Thereafter, the center pin 24 is disposed in the space 20C provided at the winding center of the wound body.

Thereafter, the wound body is interposed between the pair of insulating plates 12 and 13, and the wound body in that state is contained in the battery can 11 together with the insulating plates 12 and 13. In this case, the positive electrode lead 25 is coupled to the safety valve mechanism 15 by a method such as a welding method, and the negative electrode lead 26 is coupled to the battery can 11 by a method such as a welding method. Thereafter, the electrolytic solution is injected into the battery can 11 to thereby impregnate the wound body with the electrolytic solution, causing each of the positive electrode 21, the negative electrode 22, and the separator 23 to be impregnated with the electrolytic solution. As a result, the wound electrode body 20 is formed.

Lastly, the open end of the battery can 11 is crimped by means of the gasket 17 to thereby attach the battery cover 14, the safety valve mechanism 15, and the positive temperature coefficient device 16 to the open end of the battery can 11. Thus, the wound electrode body 20 is sealed in the battery can 11. As a result, the lithium-ion secondary battery is completed.

According to the cylindrical lithium-ion secondary battery, the electrolytic solution has a configuration similar to that of the electrolytic solution according to the embodiment of the technology described above, i.e., the electrolytic solution includes the dioxane compound. In this case, the decomposition reaction of the electrolytic solution is reduced and the generation of undesired gas is also reduced for the reason described above. Accordingly, the swelling of the lithium-ion secondary battery is suppressed, which makes it possible to achieve superior battery characteristics.

In particular, the negative electrode may include materials including, without limitation, the carbon material and the silicon-containing material. This secures a sufficient battery capacity and also sufficiently suppresses the swelling of the lithium-ion secondary battery. It is thus possible to achieve higher effects accordingly.

Other action and effects related to the cylindrical lithium-ion secondary battery are similar to those related to the electrolytic solution described above.

Next, a description is given of a laminated lithium-ion secondary battery as another example of the lithium-ion secondary battery. In the following description, the components of the cylindrical lithium-ion secondary battery described already are referred to where appropriate with reference to FIGS. 1 and 2.

Figure 3:
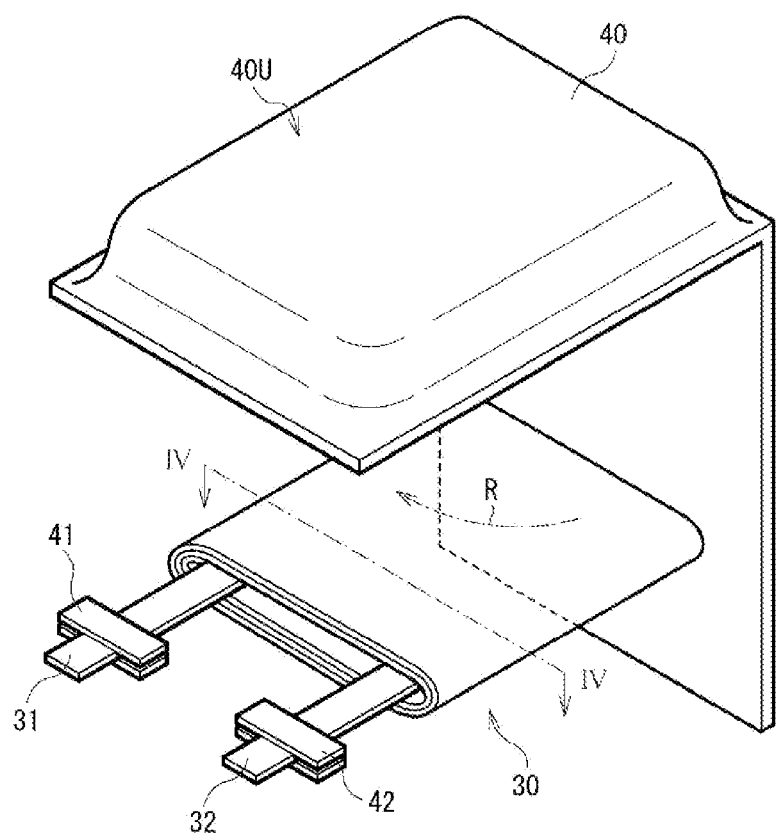
FIG. 3 is a perspective view of a configuration of another lithium-ion secondary battery (laminated-film type) according to an embodiment of the technology.
Figure 4:
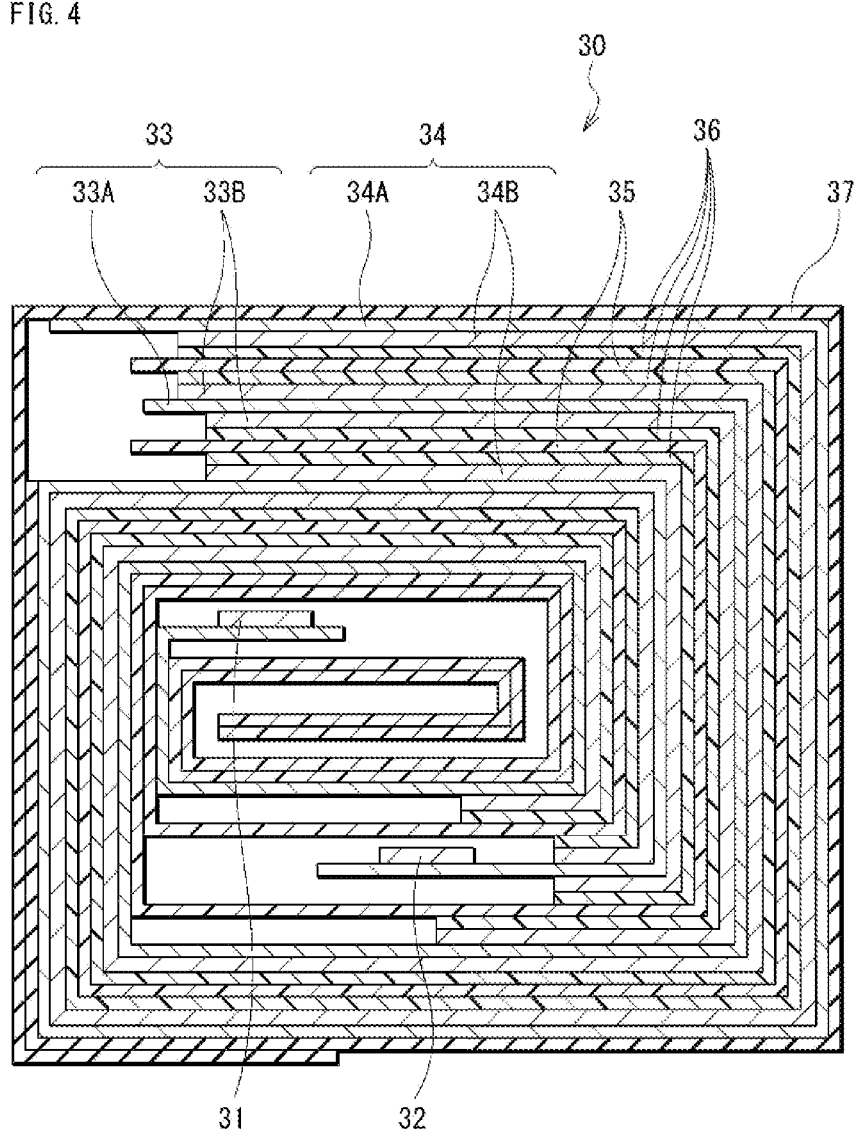
FIG. 4 is an enlarged sectional view of a configuration of a main part of the lithium-ion secondary battery illustrated in FIG. 3.

FIG. 3 is a perspective view of a configuration of another lithium-ion secondary battery. FIG. 4 illustrates, in an enlarged manner, a sectional configuration of a main part, i.e., a wound electrode body 30, of the lithium-ion secondary battery taken along a line IV-IV illustrated in FIG. 3. It should be understood that FIG. 3 illustrates a state in which the wound electrode body 30 and an outer package member 40 are separated away from each other.

Referring to FIG. 3, the lithium-ion secondary battery is provided with the outer package member 40 that has a film shape, for example. The outer package member 40 contains a battery device, i.e., the wound electrode body 30. The outer package member 40 has softness or flexibility.

The wound electrode body 30 has a structure in which a positive electrode 33 and a negative electrode 34 are stacked on each other with a separator 35 and an electrolyte layer 36 interposed therebetween and in which the positive electrode 33, the negative electrode 34, the separator 35, and the electrolyte layer 36 are wound, for example. A surface of the wound electrode body 30 is protected by means of, for example, a protective tape 37. The electrolyte layer 36 is interposed between the positive electrode 33 and the separator 35, and is also interposed between the negative electrode 34 and the separator 35, for example.

A positive electrode lead 31 is coupled to the positive electrode 33. The positive electrode lead 31 is led out from inside to outside of the outer package member 40. The positive electrode lead 31 includes a material similar to a material included in the positive electrode lead 25, for example. The positive electrode lead 31 has a shape such as a thin-plate shape or a meshed shape.

A negative electrode lead 32 is coupled to the negative electrode 34. The negative electrode lead 32 is led out from the inside to the outside of the outer package member 40. The direction in which the negative electrode lead 32 is led out is similar to that of the positive electrode lead 31, for example. The negative electrode lead 32 includes a material similar to a material included in the negative electrode lead 26, for example. The negative electrode lead 32 has a shape similar to that of the positive electrode lead 31, for example.

The outer package member 40 is, for example, a single film that is foldable in a direction of an arrow R illustrated in FIG. 3. The outer package member 40 includes a portion having a depression 40U, for example. The depression 40U is adapted to contain the wound electrode body 30.

The outer package member 40 is a stacked body or a laminated film including, for example, a fusion-bonding layer, a metal layer, and a surface protective layer that are stacked in this order from an inner side to an outer side. In a process of manufacturing the lithium-ion secondary battery, for example, the outer package member 40 is folded in such a manner that portions of the fusion-bonding layer oppose each other with the wound electrode body 30 interposed therebetween. Thereafter, outer edges of the fusion-bonding layer are fusion-bonded to each other. The fusion-bonding layer is a film that includes, for example, a polymer compound such as polypropylene. The metal layer is, for example, a metal foil that includes a metal material such as aluminum. The surface protective layer is a film that includes, for example, a polymer compound such as nylon. The outer package member 40 may include, for example, two laminated films that are adhered to each other by means of a material such as an adhesive.

A sealing film 41, for example, is interposed between the outer package member 40 and the positive electrode lead 31. The sealing film 41 is adapted to prevent entry of outside air. The sealing film 41 includes a material having adherence to the positive electrode lead 31. Examples of such a material include a polyolefin resin such as polypropylene.

A sealing film 42, for example, is interposed between the outer package member 40 and the negative electrode lead 32. The sealing film 42 has a function similar to that of the sealing film 41. A material included in the sealing film 42 is similar to the material included in the sealing film 41 except that the material included in the sealing film 42 has adherence to the negative electrode lead 32, not to the positive electrode lead 31.

The positive electrode 33 includes, for example, a positive electrode current collector 33A and a positive electrode active material layer 33B. The negative electrode 34 includes, for example, a negative electrode current collector 34A and a negative electrode active material layer 34B. The positive electrode current collector 33A, the positive electrode active material layer 33B, the negative electrode current collector 34A, and the negative electrode active material layer 34B respectively have configurations similar to those of the positive electrode current collector 21A, the positive electrode active material layer 21B, the negative electrode current collector 22A, and the negative electrode active material layer 22B, for example. The separator 35 has a configuration similar to that of the separator 23, for example.

The electrolyte layer 36 includes an electrolytic solution and a polymer compound. The electrolyte layer 36 described here is a so-called gel electrolyte in which the polymer compound holds the electrolytic solution. A reason for this is that high ionic conductivity is obtainable and leakage of the electrolytic solution is prevented. The high ionic conductivity is 1 mS/cm or higher at room temperature, for example. The electrolyte layer 36 may further include other materials including, without limitation, various additives.

A configuration of the electrolytic solution is as described above. The polymer compound includes, for example, a homopolymer, a copolymer, or both. Examples of the homopolymer include polyvinylidene difluoride. Examples of the copolymer include a copolymer of vinylidene fluoride and hexafluoropylene.

Regarding the electrolyte layer 36 which is a gel electrolyte, the concept of the solvent included in the electrolytic solution is broad and encompasses not only a liquid material but also an ion-conductive material that is able to dissociate the electrolyte salt. Accordingly, in a case of using an ion-conductive polymer compound, the polymer compound is also encompassed by the solvent.

The lithium-ion secondary battery operates as follows, for example. Upon charging the lithium-ion secondary battery, lithium ions are extracted from the positive electrode 33, and the extracted lithium ions are inserted into the negative electrode 34 via the electrolyte layer 36. Upon discharging the lithium-ion secondary battery, lithium ions are extracted from the negative electrode 34, and the extracted lithium ions are inserted into the positive electrode 33 via the electrolyte layer 36.

The lithium-ion secondary battery including the electrolyte layer 36 is manufactured by any of the following three types of procedures, for example.

[First Procedure]

First, the positive electrode 33 is fabricated by a procedure similar to that of the positive electrode 21. That is, the positive electrode 33 is fabricated by forming the positive electrode active material layers 33B on both sides of the positive electrode current collector 33A. Further, the negative electrode 34 is fabricated by a procedure similar to that of the negative electrode 22. That is, the negative electrode 34 is fabricated by forming the negative electrode active material layers 34B on both sides of the negative electrode current collector 34A.

Thereafter, the electrolytic solution is prepared, following which the prepared electrolytic solution, the polymer compound, and a material such as an organic solvent are mixed to thereby prepare a precursor solution. Thereafter, the precursor solution is applied on the positive electrode 33, following which the applied precursor solution is dried to thereby form the electrolyte layer 36. The precursor solution is also applied on the negative electrode 34, following which the applied precursor solution is dried to thereby form the electrolyte layer 36. Thereafter, the positive electrode lead 31 is coupled to the positive electrode current collector 33A by a method such as a welding method, and the negative electrode lead 32 is coupled to the negative electrode current collector 34A by a method such as a welding method. Thereafter, the positive electrode 33 and the negative electrode 34 are stacked on each other with the separator 35 and the electrolyte layer 36 interposed therebetween, following which the positive electrode 33, the negative electrode 34, the separator 35, and the electrolyte layer 36 are wound to thereby form the wound electrode body 30. Thereafter, the protective tape 37 is attached to a surface of the wound electrode body 30.

Lastly, the outer package member 40 is folded in such a manner as to sandwich the wound electrode body 30, following which the outer edges of the outer package member 40 are bonded to each other by a method such as a thermal fusion bonding method. In this case, the sealing film 41 is disposed between the outer package member 40 and the positive electrode lead 31, and the sealing film 42 is disposed between the outer package member 40 and the negative electrode lead 32. Thus, the wound electrode body 30 is sealed in the outer package member 40. As a result, the lithium-ion secondary battery is completed.

[Second Procedure]

First, the positive electrode 33 and the negative electrode 34 are fabricated. Thereafter, the positive electrode lead 31 is coupled to the positive electrode 33, and the negative electrode lead 32 is coupled to the negative electrode 34. Thereafter, the positive electrode 33 and the negative electrode 34 are stacked on each other with the separator 35 interposed therebetween, following which the positive electrode 33, the negative electrode 34, and the separator 35 are wound to thereby form a wound body. Thereafter, the protective tape 37 is attached to a surface of the wound body. Thereafter, the outer package member 40 is folded in such a manner as to sandwich the wound body, following which the outer edges excluding one side of the outer package member 40 are bonded to each other by a method such as a thermal fusion bonding method. Thus, the wound body is contained in the pouch-shaped outer package member 40.

Thereafter, the electrolytic solution, the monomers, and a polymerization initiator are mixed, following which the mixture is stirred to thereby prepare a composition for electrolyte. The monomers are raw materials of the polymer compound. Another material such as a polymerization inhibitor is mixed on an as-needed basis in addition to the electrolytic solution, the monomers, and the polymerization initiator. Thereafter, the composition for electrolyte is injected into the pouch-shaped outer package member 40, following which the outer package member 40 is sealed by a method such as a thermal fusion bonding method. Lastly, the monomers are thermally polymerized to thereby form the polymer compound. This allows the electrolytic solution to be held by the polymer compound, thereby forming the electrolyte layer 36. Thus, the wound electrode body 30 is sealed in the outer package member 40. As a result, the lithium-ion secondary battery is completed.

[Third Procedure]

First, a wound body is fabricated and the wound body is contained in the pouch-shaped outer package member 40 thereafter by a procedure similar to the second procedure, except for using the separator 35 that includes polymer compound layers provided on both sides of a base layer. Thereafter, the electrolytic solution is injected into the outer package member 40, following which an opening of the outer package member 40 is sealed by a method such as a thermal fusion bonding method. Lastly, the outer package member 40 is heated with a weight being applied to the outer package member 40 to thereby cause the separator 35 to be closely attached to each of the positive electrode 33 and the negative electrode 34 with the polymer compound layer interposed therebetween. The polymer compound layer is thereby impregnated with the electrolytic solution and the polymer compound layer is gelated, forming the electrolyte layer 36. Thus, the wound electrode body 30 is sealed in the outer package member 40. As a result, the lithium-ion secondary battery is completed.

The third procedure helps to reduce swelling of the lithium-ion secondary battery, in contrast to the first procedure. The third procedure also helps to prevent the solvent and the monomers, which are the raw materials of the polymer compound, from remaining in the electrolyte layer 36, in contrast to the second procedure. Accordingly, the electrolyte layer 36 is sufficiently closely attached to each of the positive electrode 33, the negative electrode 34, and the separator 35.

According to the laminated lithium-ion secondary battery, the electrolytic solution included in the electrolyte layer 36 has a configuration similar to that of the electrolytic solution according to the embodiment of the technology described above, i.e., the electrolytic solution includes the dioxane compound. Accordingly, it is possible to achieve superior battery characteristics for a reason similar to that of the cylindrical lithium-ion secondary battery. Other action and effects related to the laminated lithium-ion secondary battery are similar to those related to the cylindrical lithium-ion secondary battery.

The laminated lithium-ion secondary battery may include the electrolytic solution instead of the electrolyte layer 36. In this case, the wound electrode body 30 is impregnated with the electrolytic solution; thus, each of the positive electrode 33, the negative electrode 34, and the separator 35 is impregnated with the electrolytic solution. Further, the wound body is contained in the pouch-shaped outer package member 40, following which the electrolytic solution is injected into the pouch-shaped outer package member 40 to thereby impregnate the wound body with the electrolytic solution. As a result, the wound electrode body 30 is formed. Similar effects are also obtainable in this case.

Examples of applications of the lithium-ion secondary battery are as described below. It should be understood that applications of the electrolytic solution are similar to those of the lithium-ion secondary battery. Accordingly, the applications of the electrolytic solution are described below together with the applications of the lithium-ion secondary battery.

The applications of the lithium-ion secondary battery are not particularly limited as long as they are, for example, machines, apparatuses, instruments, devices, or systems (assembly of a plurality of apparatuses, for example) in which the lithium-ion secondary battery is usable as a driving power source, an electric power storage source for electric power accumulation, or any other source. The lithium-ion secondary battery used as a power source may serve as a main power source or an auxiliary power source. The main power source is preferentially used regardless of the presence of any other power source. The auxiliary power source may be used in place of the main power source, or may be switched from the main power source on an as-needed basis. In a case where the lithium-ion secondary battery is used as the auxiliary power source, the kind of the main power source is not limited to the lithium-ion secondary battery.

Examples of the applications of the lithium-ion secondary battery include: electronic apparatuses including portable electronic apparatuses: portable life appliances: storage devices: electric power tools: battery packs mountable on laptop personal computers or other apparatuses as a detachable power source; medical electronic apparatuses: electric vehicles; and electric power storage systems. Examples of the electronic apparatuses include video cameras, digital still cameras, mobile phones, laptop personal computers, cordless phones, headphone stereos, portable radios, portable televisions, and portable information terminals. Examples of the portable life appliances include electric shavers. Examples of the storage devices include backup power sources and memory cards. Examples of the electric power tools include electric drills and electric saws. Examples of the medical electronic apparatuses include pacemakers and hearing aids. Examples of the electric vehicles include electric automobiles including hybrid automobiles. Examples of the electric power storage systems include home battery systems for accumulation of electric power for emergency. Needless to say, the lithium-ion secondary battery may have applications other than those described above.

EXAMPLES

A description is given of Examples of the technology.

Experiment Examples 1-1 to 1-19

The laminated lithium-ion secondary batteries illustrated in FIGS. 3 and 4 were fabricated and their respective battery characteristics were evaluated as described below.

In a case of fabricating the positive electrode 33, first, 91 parts by mass of the positive electrode active material (lithium cobalt oxide ($LiCoO_2$)), 3 parts by mass of the positive electrode binder (polyvinylidene difluoride), and 6 parts by mass of the positive electrode conductor (graphite) were mixed with each other to thereby obtain a positive electrode mixture. Thereafter, the positive electrode mixture was put into an organic solvent (N-methyl-2-pyrrolidone), following which the organic solvent was stirred to thereby prepare a paste positive electrode mixture slurry. Thereafter, the positive electrode mixture slurry was applied on both sides of the positive electrode current collector 33A (a band-shaped aluminum foil having a thickness of 12 μm) by means of a coating apparatus, following which the applied positive electrode mixture slurry was dried to thereby form the positive electrode active material layers 33B. Lastly, the positive electrode active material layers 33B were compression-molded by means of a roll pressing machine.

In a case of fabricating the negative electrode 34, first, 97 parts by mass of the negative electrode active material (graphite serving as a carbon material and having a median diameter D50 of 15 μm), 1.5 parts by mass of the negative electrode binder (an acrylic acid-modified styrene-butadiene copolymer), and 1.5 parts by mass of a thickener (carboxymethyl cellulose) were mixed with each other to thereby obtain a negative electrode mixture. Thereafter, the negative electrode mixture was put into an aqueous solvent (pure water), following which the organic solvent was stirred to thereby prepare a paste negative electrode mixture slurry. Thereafter, the negative electrode mixture slurry was applied on both sides of the negative electrode current collector 34A (a band-shaped copper foil having a thickness of 15 μm) by means of a coating apparatus, following which the applied negative electrode mixture slurry was dried to thereby form the negative electrode active material layers 34B. Lastly, the negative electrode active material layers 34B were compression-molded by means of a roll pressing machine.

In a case of preparing the electrolytic solution, the electrolyte salt (lithium hexafluorophosphate) was added to a solvent (ethylene carbonate, propylene carbonate, ethylmethyl carbonate, and propyl propionate), following which the solvent was stirred. In this case, a mixture ratio (a weight ratio) in the solvent of ethylene carbonate:propylene carbonate:ethylmethyl carbonate:propyl propionate was set to 30:10:40:20, and the content of the electrolyte salt with respect to the solvent was set to 1.2 mol/kg. Thereafter, the dioxane compound was added to the solvent, following which the solvent was stirred. The kinds of the dioxane compound and the contents (wt %) of the dioxane compound in the electrolytic solution were as described in Table 1.

For comparison, electrolytic solutions were prepared in accordance with a similar procedure except that other compounds were used instead of the dioxane compound. The kinds of the other compounds and the contents of the other compounds in the electrolytic solution were as described in Table 1.

In a case of assembling the lithium-ion secondary battery, first, the positive electrode lead 31 including aluminum was welded to the positive electrode current collector 33A, and the negative electrode lead 32 including copper was welded to the negative electrode current collector 34A. Thereafter, the positive electrode 33 and the negative electrode 34 were stacked on each other with the separator 35 interposed therebetween to thereby obtain a stacked body. Thereafter, the stacked body was wound, following which the protective tape 37 was attached to the stacked body to thereby obtain a wound body.

As the separator 35, a base layer provided with polymer compound layers on both sides thereof was used. In a case of fabricating the separator 35, first, a polymer compound (polyvinylidene difluoride) and inorganic particles (an aluminum oxide having a median diameter D50 of 0.3 μm) were added to an organic solvent (N-methyl-2-pyrrolidone), following which the organic solvent was stirred to thereby obtain a dispersion liquid. In this case, a mixture ratio (weight ratio) of the polymer compound to the inorganic particles was set to 20:80. Thereafter, the base layer (a fine-porous polyethylene film having a thickness of 12 μm) was immersed in the dispersion liquid. Thereafter, the base layer was taken out from the dispersion liquid, following which the organic solvent was removed using an aqueous solvent (pure water). Lastly, the base layer was dried using hot air having a temperature of 80° C. The polymer compound layers (having a total thickness of 5 μm) were thereby formed on both sides of the base layer to thereby obtain the separator 35.

Thereafter, the outer package member 40 was folded in such a manner as to sandwich the wound body, following which the outer edges of two sides of the outer package member 40 were thermal fusion bonded to each other. As the outer package member 40, an aluminum laminated film was used in which a surface protective layer (a nylon film having a thickness of 25 μm), a metal layer (an aluminum foil having a thickness of 40 μm), and a fusion-bonding layer (a polypropylene film having a thickness of 30 μm) were stacked in this order. In this case, the sealing film 41 (a polypropylene film) was interposed between the outer package member 40 and the positive electrode lead 31, and the sealing film 42 (a polypropylene film) was interposed between the outer package member 40 and the negative electrode lead 32.

Lastly, the electrolytic solution was injected into the outer package member 40 to thereby impregnate the wound body with the electrolytic solution, and thereafter, the outer edges of one of the remaining sides of the outer package member 40 were thermal fusion bonded to each other in a reduced-pressure environment. Thus, the wound electrode body 30 was formed, being sealed in the outer package member 40. As a result, the laminated lithium-ion secondary battery was completed.

Evaluation of a battery characteristic of the lithium-ion secondary batteries revealed the results described in Table 1. A swelling characteristic was evaluated here as the battery characteristic.

In a case of examining the swelling characteristic, first, the lithium-ion secondary battery was charged and discharged for two cycles in an ambient-temperature environment (at a temperature of 23° C.) in order to stabilize a state of the lithium-ion secondary battery. Upon charging, the lithium-ion secondary battery was charged with a constant current of 0.2 C until the voltage reached 4.45 V, and was thereafter charged with a constant voltage of 4.45 V until the current reached 0.05 C. Upon discharging, the lithium-ion secondary battery was discharged with a constant current of 0.2 C until the voltage reached 2.5 V. It should be understood that 0.2 C and 0.05 C are values of currents that cause battery capacities (theoretical capacities) to be completely discharged in 5 hours and 20 hours, respectively.

Thereafter, the lithium-ion secondary battery was charged in the same environment, following which a thickness (a pre-storage thickness (mm)) of the charged lithium-ion secondary battery was measured. Charging conditions were as described above.

Thereafter, the charged lithium-ion secondary battery was stored (for a storing time of 150 hours) in a high-temperature environment (at a temperature of 75° C.), following which the thickness (a post-storage thickness (mm)) of the charged lithium-ion secondary battery was measured.

Lastly, a swelling rate (%)=[(post-storage thickness−pre-storage thickness)/pre-storage thickness]×100 was calculated.

compound (Experiment example 1-16). More specifically, a percentage reduction in the swelling rate was only about 22% at a maximum.

In contrast, in a case where the electrolytic solution included the dioxane compound (the first dioxane compound and the second dioxane compound) (Experiment examples 1-1 to 1-15), the swelling rate markedly decreased as compared to the case where the electrolytic solution did not include the other compound (Experiment example 1-16). More specifically, the percentage reduction in the swelling rate reached about 41% at a maximum.

In other words, the percentage reduction in the swelling rate in the case where the electrolytic solution included the dioxane compound was about twice the percentage reduction in the swelling rate in the case where the electrolytic solution did not include the dioxane compound.

In particular, in the case where the electrolytic solution included the dioxane compound, the swelling rate sufficiently decreased if the content of the first dioxane compound in the electrolytic solution was greater than or equal to 0.001 wt % and less than or equal to 5 wt % and the content of the second dioxane compound in the electrolytic solution was greater than or equal to 0.001 wt % and less than or equal to 5 wt %.

Experiment Examples 2-1 to 2-36

As described in Tables 2 to 4, in accordance with a similar procedure except that an additive was added to the electrolytic solution, the lithium-ion secondary batteries were fab-

TABLE 1

(Negative electrode active material: graphite)

| Experiment example | First dioxane compound Kind | First dioxane compound Content (wt %) | Second dioxane compound Kind | Second dioxane compound Content (wt %) | Other compound Kind | Other compound Content (wt %) | Swelling rate (%) |
|---|---|---|---|---|---|---|---|
| 1-1 | Formula (1-1) | 0.001 | — | — | — | — | 118 |
| 1-2 | | 0.01 | | | | | 111 |
| 1-3 | | 0.1 | | | | | 109 |
| 1-4 | | 1 | | | | | 110 |
| 1-5 | | 5 | | | | | 125 |
| 1-6 | Formula (1-8) | 0.001 | — | — | — | — | 120 |
| 1-7 | | 0.01 | | | | | 112 |
| 1-8 | | 0.1 | | | | | 109 |
| 1-9 | | 1 | | | | | 111 |
| 1-10 | | 5 | | | | | 129 |
| 1-11 | — | — | Formula (2-3) | 0.001 | — | — | 119 |
| 1-12 | | | | 0.01 | | | 112 |
| 1-13 | | | | 0.1 | | | 109 |
| 1-14 | | | | 1 | | | 112 |
| 1-15 | | | | 5 | | | 130 |
| 1-16 | — | — | — | — | — | — | 185 |
| 1-17 | — | — | — | — | Formula (3-1) | 1 | 149 |
| 1-18 | — | — | — | — | Formula (3-2) | 1 | 145 |
| 1-19 | — | — | — | — | Formula (3-3) | 1 | 190 |

As described in Table 1, the swelling rate varied greatly depending on the configuration of the electrolytic solution.

Specifically, in a case where the electrolytic solution included the other compound (Experiment examples 1-17 to 1-19), the swelling rate decreased only slightly, and the swelling rate increased in some cases, as compared with a case where the electrolytic solution did not include the other ricated with use of the dioxan compound, following which the battery characteristics of the lithium-ion secondary batteries were examined.

As the additive (the solvent), an unsaturated cyclic carbonate ester (vinylene carbonate (VC)), a halogenated carbonate ester (4-fluoro-1,3-dioxolane-2-one (FEC)), and a dinitrile compound (succinonitrile (SN)) were used. As the additive (the electrolyte salt), lithium tetrafluoroborate (LiBF$_4$), lithium difluorophosphate (LiPF$_2$O$_2$), and lithium bis(oxalato)borate (LiC$_4$BO$_8$ (LiBOB)) were used. The contents (wt %) of the additives in the electrolytic solution were as described in Tables 2 to 4.

As the battery characteristics, a cyclability characteristic was also examined in addition to the swelling characteristic. In a case of examining the cyclability characteristic, first, a state of the lithium-ion secondary battery was stabilized in accordance with the above-described procedure, following which the lithium-ion secondary battery was charged and discharged in an ambient-temperature environment (at a temperature of 23° C.), to thereby measure a third-cycle discharge capacity. Thereafter, the lithium-ion secondary battery was charged and discharged for 100 cycles in the same environment, following which a 103rd-cycle discharge capacity was measured. Lastly, a capacity retention rate (%)=(103rd-cycle discharge capacity/third-cycle discharge capacity)×100 was calculated. Charging and discharging conditions were similar to those in the case of examining the swelling characteristic.

TABLE 2

(Negative electrode active material: graphite)

| Experiment example | First dioxane compound Kind | Content (wt %) | Additive Kind | Content (wt %) | Swelling rate (%) | Capacity retention rate (%) |
|---|---|---|---|---|---|---|
| 1-1 | Formula (1-1) | 0.001 | — | — | 118 | 88 |
| 2-1 | | | VC | 1 | 120 | 92 |
| 2-2 | | | FEC | 2 | 122 | 92 |
| 2-3 | | | SN | 2 | 115 | 90 |
| 2-4 | | | LiBF$_4$ | 1 | 119 | 90 |
| 2-5 | | | LiPF$_2$O$_2$ | 1 | 117 | 91 |
| 2-6 | | | LiBOB | 1 | 124 | 92 |
| 1-4 | Formula (1-1) | 1 | — | — | 110 | 87 |
| 2-7 | | | VC | 1 | 111 | 92 |
| 2-8 | | | FEC | 2 | 114 | 92 |
| 2-9 | | | SN | 2 | 105 | 90 |
| 2-10 | | | LiBF$_4$ | 1 | 110 | 90 |
| 2-11 | | | LiPF$_2$O$_2$ | 1 | 108 | 91 |
| 2-12 | | | LiBOB | 1 | 114 | 91 |

TABLE 3

(Negative electrode active material: graphite)

| Experiment example | First dioxane compound Kind | Content (wt %) | Additive Kind | Content (wt %) | Swelling rate (%) | Capacity retention rate (%) |
|---|---|---|---|---|---|---|
| 1-6 | Formula (1-8) | 0.001 | — | — | 120 | 89 |
| 2-13 | | | VC | 1 | 121 | 92 |
| 2-14 | | | FEC | 2 | 126 | 92 |
| 2-15 | | | SN | 2 | 118 | 91 |
| 2-16 | | | LiBF$_4$ | 1 | 122 | 91 |
| 2-17 | | | LiPF$_2$O$_2$ | 1 | 120 | 91 |
| 2-18 | | | LiBOB | 1 | 128 | 92 |
| 1-9 | Formula (1-8) | 1 | — | — | 111 | 88 |
| 2-19 | | | VC | 1 | 112 | 92 |
| 2-20 | | | FEC | 2 | 116 | 92 |
| 2-21 | | | SN | 2 | 107 | 91 |
| 2-22 | | | LiBF$_4$ | 1 | 112 | 92 |
| 2-23 | | | LiPF$_2$O$_2$ | 1 | 111 | 92 |
| 2-24 | | | LiBOB | 1 | 115 | 92 |

TABLE 4

(Negative electrode active material: graphite)

| Experiment example | Second dioxane compound Kind | Content (wt %) | Additive Kind | Content (wt %) | Swelling rate (%) | Capacity retention rate (%) |
|---|---|---|---|---|---|---|
| 1-11 | Formula (2-3) | 0.001 | — | — | 119 | 90 |
| 2-25 | | | VC | 1 | 120 | 92 |
| 2-26 | | | FEC | 2 | 125 | 93 |
| 2-27 | | | SN | 2 | 118 | 91 |
| 2-28 | | | LiBF$_4$ | 1 | 121 | 91 |
| 2-29 | | | LiPF$_2$O$_2$ | 1 | 120 | 92 |
| 2-30 | | | LiBOB | 1 | 126 | 92 |
| 1-14 | Formula (2-3) | 1 | — | — | 112 | 90 |
| 2-31 | | | VC | 1 | 112 | 93 |
| 2-32 | | | FEC | 2 | 115 | 93 |
| 2-33 | | | SN | 2 | 108 | 92 |
| 2-34 | | | LiBF$_4$ | 1 | 113 | 92 |
| 2-35 | | | LiPF$_2$O$_2$ | 1 | 111 | 93 |
| 2-36 | | | LiBOB | 1 | 115 | 93 |

As described in Tables 2 to 4, in a case where the electrolytic solution included the additive (Experiment examples 2-1 to 2-36), the capacity retention rate increased while the swelling rate sufficiently decreased as compared with the case where the electrolytic solution did not include the additive (Experiment examples 1-1, 1-4, 1-6, 1-9, 1-11, and 1-14). In particular, in a case where the electrolytic solution included the dinitrile compound, the capacity retention rate increased while the swelling rate decreased.

Experiment Examples 3-1 to 3-19

As described in Table 5, in accordance with a similar procedure except that a kind of the negative electrode active material was changed, the lithium-ion secondary batteries were fabricated using the dioxane compound, following which the battery characteristics of the lithium-ion secondary batteries were examined. Here, a silicon-containing material (a simple substance of silicon) was used instead of the carbon material (graphite) as the negative electrode active material.

In the case of fabricating the negative electrode 34, first, 90 parts by mass of the negative electrode active material (silicon having a median diameter D50 of 1 μm), 5 parts by mass of a polyimide precursor, and 5 parts by mass of the negative electrode conductor (graphite) were mixed with each other to thereby obtain a negative electrode mixture. Thereafter, the negative electrode mixture was put into an organic solvent (N-methyl-2-pyrrolidone), following which the organic solvent was stirred to thereby prepare a paste negative electrode mixture slurry. Thereafter, the negative electrode mixture slurry was applied on both sides of the negative electrode current collector 34A (a band-shaped copper foil having a thickness of 15 μm) by means of a coating apparatus, following which a coating of the negative electrode mixture slurry was dried. Thereafter, the coating was compression-molded by means of a roll pressing machine. Lastly, the coating was heated at a heating temperature of 400° ° C. for 12 hours in a vacuum atmosphere. As a result, the negative electrode binder (polyimide) was formed, thereby forming the negative electrode active material layer 34B.

TABLE 5

| | (Negative electrode active material: silicon) | | | | | | |
|---|---|---|---|---|---|---|---|
| | First dioxane compound | | Second dioxane compound | | Other compound | | |
| Experiment example | Kind | Content (wt %) | Kind | Content (wt %) | Kind | Content (wt %) | Swelling rate (%) |
| 3-1 | Formula (1-1) | 0.001 | — | — | — | — | 134 |
| 3-2 | | 0.01 | | | | | 132 |
| 3-3 | | 0.1 | | | | | 127 |
| 3-4 | | 1 | | | | | 133 |
| 3-5 | | 5 | | | | | 144 |
| 3-6 | Formula (1-8) | 0.001 | — | — | — | — | 142 |
| 3-7 | | 0.01 | | | | | 135 |
| 3-8 | | 0.1 | | | | | 130 |
| 3-9 | | 1 | | | | | 133 |
| 3-10 | | 5 | | | | | 148 |
| 3-11 | — | — | Formula (2-3) | 0.001 | — | — | 143 |
| 3-12 | | | | 0.01 | | | 135 |
| 3-13 | | | | 0.1 | | | 133 |
| 3-14 | | | | 1 | | | 134 |
| 3-15 | | | | 5 | | | 148 |
| 3-16 | — | — | — | — | — | — | 202 |
| 3-17 | — | — | — | — | Formula (3-1) | 1 | 178 |
| 3-18 | — | — | — | — | Formula (3-2) | 1 | 175 |
| 3-19 | — | — | — | — | Formula (3-3) | 1 | 210 |

As described in Table 5, also in the case where the silicon-containing material was used as the negative electrode active material, similar results as those in the case where the carbon material was used as the negative electrode active material (Table 1) were obtained.

In other words, in the case where the electrolytic solution included the other compound (Experiment examples 3-17 to 3-19), the swelling rate decreased only slightly, and the swelling rate increased in some cases, as compared with the case where the electrolytic solution did not include the other compound (Experiment example 3-16). In contrast, in the case where the electrolytic solution included the dioxane compound (Experiment examples 3-1 to 3-15), the swelling rate greatly decreased as compared with the case where the electrolytic solution did not include the dioxane compound (Experiment example 3-16).

More specifically, the percentage reduction in the swelling rate in the case where the electrolytic solution included the other compound was about 13% at a maximum, while percentage reduction in the swelling rate in the case where the electrolytic solution included the dioxane compound reached about 37% at a maximum. In other words, the percentage reduction in the swelling rate in the case where the electrolytic solution included the dioxane compound was about three times the percentage reduction in the swelling rate in the case where the electrolytic solution did not include the dioxane compound.

Based upon the results described in Tables 1 to 5, the inclusion of the dioxane compound in the electrolytic solution improved the swelling characteristic of the lithium-ion secondary battery. Accordingly, a superior battery characteristic of the lithium-ion secondary battery was obtained.

Although the technology has been described above with reference to some embodiments and Examples, embodiments of the technology are not limited to those described with reference to the embodiments and the Examples above and are modifiable in a variety of ways.

Specifically, although the description has been given of the laminated lithium-ion secondary battery, this is non-limiting. For example, the lithium-ion secondary battery may be of any other type such as a cylindrical type, a prismatic type, or a coin type.

Moreover, although the description has been given of a case of the battery device to be used in the lithium-ion secondary battery having a wound structure, this is non-limiting. For example, the battery device may have any other structure such as a stacked structure.

It should be understood that an application of the above-described electrolytic solution is not limited to the lithium-ion secondary battery, and the electrolytic solution may be used for other applications. Examples of the other applications include other electrochemical devices such as capacitors.

The effects described herein are mere examples, and effects of the technology are therefore not limited to those described herein. Accordingly, the technology may achieve any other effect.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention claimed is:
1. A lithium-ion secondary battery comprising:
a positive electrode;
a negative electrode; and
an electrolytic solution that includes: a solvent; an electrolyte salt; and at least one of a first dioxane compound or a second dioxane compound,
wherein the first dioxane compound is represented by Formula (1), and the second dioxane compound is represented by Formula (2),

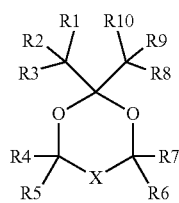

(1)

wherein
each of R1 to R10 includes a hydrogen group or a monovalent hydrocarbon group, and
X includes a divalent hydrocarbon group, and

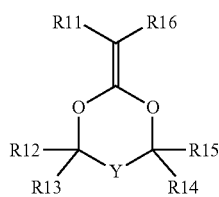

(2)

wherein
each of R11 to R16 includes a hydrogen group or a monovalent hydrocarbon group, and
Y includes a divalent hydrocarbon group, and
wherein
a content of the first dioxane compound in the electrolytic solution is from 0.001 weight percent to 5 weight percent, and
a content of the second dioxane compound in the electrolytic solution is from 0.001 weight percent to 5 weight percent.

2. The lithium-ion secondary battery according to claim 1, wherein
the monovalent hydrocarbon group includes one of an alkyl group, an alkenyl group, and an alkynyl group, and has carbon number of less than or equal to 4, and
the divalent hydrocarbon group includes one of an alkylene group, an alkenylene group, and an alkynylene group, and has carbon number of less than or equal to 4.

3. The lithium-ion secondary battery according to claim 2, wherein
the solvent includes at least one of an unsaturated cyclic carbonate ester, a halogenated carbonate ester, or a dinitrile compound, and
the electrolyte salt includes at least one of lithium tetrafluoroborate ($LiBF_4$), lithium difluorophosphate ($LiPF_2O_2$), or lithium bis(oxalato)borate ($LiC_4BO_8$).

4. The lithium-ion secondary battery according to claim 3, wherein the negative electrode includes one or both of a carbon material and a silicon-containing material.

5. The lithium-ion secondary battery according to claim 2, wherein the negative electrode includes one or both of a carbon material and a silicon-containing material.

6. The lithium-ion secondary battery according to claim 1, wherein
the solvent includes at least one of an unsaturated cyclic carbonate ester, a halogenated carbonate ester, or a dinitrile compound, and
the electrolyte salt includes at least one of lithium tetrafluoroborate ($LiBF_4$), lithium difluorophosphate ($LiPF_2O_2$), or lithium bis(oxalato)borate ($LiC_4BO_8$).

7. The lithium-ion secondary battery according to claim 6, wherein the negative electrode includes one or both of a carbon material and a silicon-containing material.

8. The lithium-ion secondary battery according to claim 1, wherein the negative electrode includes one or both of a carbon material and a silicon-containing material.

9. An electrolytic solution for a lithium-ion secondary battery, the electrolytic solution comprising:
a solvent;
an electrolyte salt; and
at least one of a first dioxane compound or a second dioxane compound,
wherein the first dioxane compound is represented by Formula (1), and the second dioxane compound is represented by Formula (2),

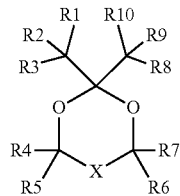

(1)

wherein
each of R1 to R10 includes a hydrogen group or a monovalent hydrocarbon group, and
X includes a divalent hydrocarbon group,

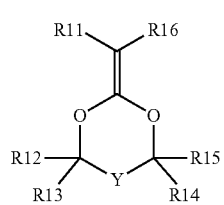

(2)

wherein
each of R11 to R16 includes a hydrogen group or a monovalent hydrocarbon group, and
Y includes a divalent hydrocarbon group, and
wherein
a content of the first dioxane compound in the electrolytic solution is from 0.001 weight percent to 5 weight percent, and
a content of the second dioxane compound in the electrolytic solution is from 0.001 weight percent to 5 weight percent.

* * * * *